(12) United States Patent
Spataro et al.

(10) Patent No.: US 11,850,381 B2
(45) Date of Patent: Dec. 26, 2023

(54) INTRAVENOUS THERAPY SYSTEM HAVING A NEEDLE HUB AND CATHETER HUB

(71) Applicant: Becton, Dickinson and Company, Franklin Lakes, NJ (US)

(72) Inventors: Joseph Spataro, Cottonwood Heights, UT (US); Kathryn Willybiro, Park City, UT (US); Huy Tran, Riverton, UT (US); Yiping Ma, Layton, UT (US); Bart D. Peterson, Farmington, UT (US); Jeffrey C. O'Bryan, Murray, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 81 days.

(21) Appl. No.: 16/743,634

(22) Filed: Jan. 15, 2020

(65) Prior Publication Data
US 2020/0230366 A1   Jul. 23, 2020

Related U.S. Application Data

(60) Provisional application No. 62/794,426, filed on Jan. 18, 2019.

(51) Int. Cl.
*A61M 25/06* (2006.01)
*A61M 25/04* (2006.01)
(Continued)

(52) U.S. Cl.
CPC .... *A61M 25/0606* (2013.01); *A61M 25/0009* (2013.01); *A61M 25/04* (2013.01);
(Continued)

(58) Field of Classification Search
CPC .............. A61M 25/0606; A61M 25/04; A61M 2025/0253; A61M 2039/0297;
(Continued)

(56) References Cited

U.S. PATENT DOCUMENTS 4,496,348 A * 1/1985 Genese ............. A61M 25/0606
                                             604/167.02
5,049,132 A * 9/1991 Shaffer ............. A61M 16/0456
                                             604/101.02
(Continued)

FOREIGN PATENT DOCUMENTS

EP       2522307       11/2012
WO    03/066126       8/2003
(Continued)

*Primary Examiner* — Katherine H Schwiker
*Assistant Examiner* — Robert F Allen
(74) *Attorney, Agent, or Firm* — Kirton McConkie; Whitney Blair; Kevin Stinger (57) ABSTRACT

An intravenous therapy system may include a housing to house an actuation hub, the actuation hub comprising; a needle hub operatively coupled to a needle to insert the needle into a patient's body; and a catheter hub operatively coupled to a catheter to insert the catheter into a patient's body, the catheter being formed coaxially with an outer surface of the needle; and an inflatable bladder formed along a length of the catheter to maintain the catheter in the patient's body.

11 Claims, 9 Drawing Sheets

(51) Int. Cl.
*A61M 25/02* (2006.01)
*A61M 25/00* (2006.01)

(52) U.S. Cl.
CPC .... *A61M 25/0631* (2013.01); *A61M 25/0693* (2013.01); *A61M 2025/0253* (2013.01)

(58) Field of Classification Search
CPC .......... A61M 2005/1586; A61M 5/158; A61M 25/0097; A61M 2005/1581; A61M 2005/1587; A61M 2005/1585; A61M 39/0247; A61M 25/0631
See application file for complete search history.

(56) References Cited

U.S. PATENT DOCUMENTS

| | | | |
|---|---|---|---|
| 6,949,084 B2 * | 9/2005 | Marggi | A61M 25/0097 604/174 |
| 8,202,253 B1 * | 6/2012 | Wexler | A61M 25/0693 604/161 |
| 2003/0163147 A1 * | 8/2003 | Rabiner | A61B 17/22012 606/159 |
| 2004/0158207 A1 * | 8/2004 | Hunn | A61M 39/02 604/164.01 |
| 2007/0191771 A1 | 8/2007 | Moyer | |
| 2009/0171282 A1 | 7/2009 | Pipenhagen et al. | |
| 2009/0177263 A1 | 7/2009 | Viller | |
| 2014/0074031 A1 * | 3/2014 | Bornhoft | A61M 39/10 604/164.01 |
| 2015/0025503 A1 * | 1/2015 | Searle | G16H 20/13 604/67 |
| 2016/0213896 A1 | 7/2016 | Bacallao | |

FOREIGN PATENT DOCUMENTS

| | | | |
|---|---|---|---|
| WO | 03066125 A2 | 8/2003 | |
| WO | 2007/005734 | 1/2007 | |
| WO | 2011/055308 | 5/2011 | |
| WO | WO-2011055308 A1 * | 5/2011 | ......... A61M 25/0017 |
| WO | 2017/158081 | 9/2017 | |

* cited by examiner

INTRAVENOUS THERAPY SYSTEM HAVING A NEEDLE HUB AND CATHETER HUB

RELATED APPLICATIONS

This application claims the benefit of U.S. Provisional Patent Application No. 62/794,426, filed Jan. 18, 2019, and entitled DIRECT PORT CATHETER AND METHODS, which is incorporated herein in its entirety.

BACKGROUND

Some intravenous therapy systems may include a straight needle and catheter axially formed around the straight needle. These intravenous therapy systems may be used for a variety of infusion therapies. For example, intravenous therapy systems may be used for infusing fluids, such as a saline solution, various medicaments, and parenteral nutrition, into a patient intravenous therapy systems may also be used for withdrawing blood from the patient. To facilitate insertion into a body, the needle of the intravenous therapy system includes a distal tip that includes a bevel used to interface with a skin of a patient as the bevel faces away from skin of the patient.

During operation of these intravenous therapy systems, the bevel formed on a distal end of the needle may cause the distal end of the needle to "dive" deeper into the patient even when the insertion angle of the intravenous therapy system remains constant. In order to complete the insertion process of the intravenous therapy system, the clinician may lower the angle of the intravenous therapy system relative to the patient so as to combat the needle diving further into the body of the patient. This maneuvering of the intravenous therapy system by the clinician, however, has limited effect in smaller gauge needles and catheters (e.g. 20-gauge, 22-gauge, and 24-gauge) because, as the gauge of the needle increases, the needle bends relatively easier when the insertion angle is lowered. The distal end of the needle may then be positioned at about a 20-degree angle within the vein and may not straighten out. The distal end of the needle digging into the back wall of the patient's blood vessel may cause blood vessel trauma, inflammation, phlebitis, among other medical conditions. This is also an issue when drawing blood with the distal end of the needle suctioned against the vein wall when a vacuum within the intravenous therapy system is created. This creation of the vacuum may further cause the distal end of the needle to become clogged and, thereby prevent fluids to pass through the needle and/or catheter of the intravenous therapy system.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous therapy system and related systems and methods. In some embodiments, an intravenous therapy system provides for the access of a patient's blood vessels in such a way as to avoid any additional physical and mental trauma to the patient apart from an initial insertion of the intravenous therapy system into the patient's blood vessel. The intravenous therapy system may include a housing to house an actuation hub, the actuation hub comprising; a needle hub operatively coupled to a needle to insert the needle into a patient's body; and a catheter hub operatively coupled to a catheter to insert the catheter into a patient's body, the catheter being formed coaxially with an outer surface of the needle; and an inflatable bladder formed along a length of the catheter to maintain the catheter in the patient's body. In an embodiment, the intravenous therapy may include a bladder fluid injection port to couple a fluid reservoir to the bladder via a length of tubing. The intravenous therapy system may also include an infusion tube fluidically coupled to the catheter to provide an infusion through the catheter and into a blood vessel within the patient's body in some embodiments. In some embodiments, the intravenous therapy system may also include a visual indicator to indicate when the needle and catheter has accessed a blood vessel within the patient's body. In some embodiments, the intravenous therapy system includes an adhesive formed on a bottom surface of the housing to secure the intravenous therapy system to a skin of the patient with an accompanying adhesive-defeating port to receive an adhesive-defeating fluid to reduce the adhesive effects of the adhesive during removal of the intravenous therapy system from the patient's skin. The intravenous therapy system, in some embodiments, may also include a window to allow a clinician implementing the intravenous therapy system to see through the housing and to a patient's skin. To facilitate actuation of the intravenous therapy system, the intravenous therapy system may include, in some embodiments, a bistable locking mechanism that selectively locks and unlocks the needle hub and catheter hub in an actuated position.

The present disclosure further relates to a method of manufacturing an intravenous device. The method may include, in some embodiments, forming a needle hub and a catheter hub within a housing; mechanically coupling a catheter to the catheter hub; mechanically coupling a needle to the needle hub; mechanically coupling a bladder to the catheter; and coupling an infusing fluidic tube to the needle and catheter.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

Figure 1:
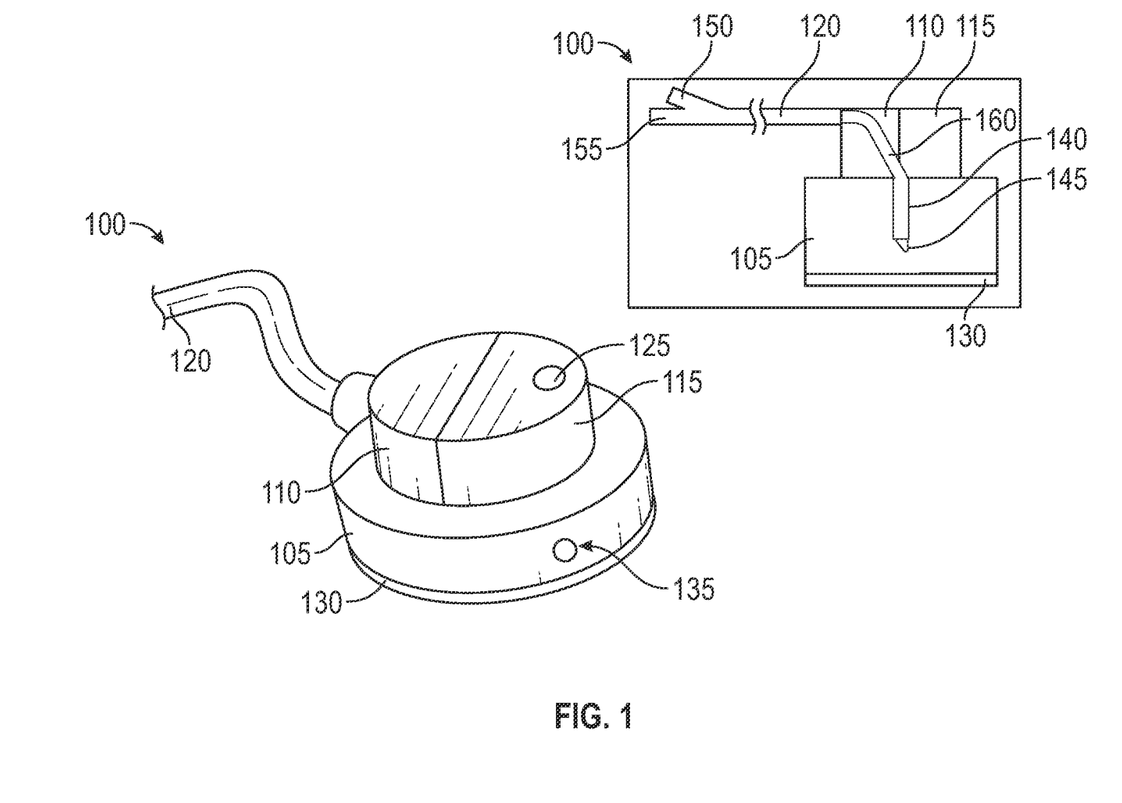
FIG. 1 is a perspective view and side, cross-sectional view of an intravenous therapy system according to an embodiment of the present disclosure.

FIG. 1 is a perspective view and side, cross-sectional view of an intravenous therapy system 100 according to an embodiment of the present disclosure. The intravenous therapy system 100 may include a housing 105 that forms a rigid casing used to house the components of the intravenous therapy system 100. The housing 105, in an embodiment, may be made of a plastic that reduces the weight of the intravenous therapy system 100. In an embodiment, a portion of the housing 105 may be made of a translucent plastic that allows a clinician or other health care provider (HCP) to see through a portion of the intravenous therapy system 100 and to the skin or surface of a patient's body. In this embodiment, the translucent plastic may specifically allow the clinician to align the intravenous therapy system 100 over a blood vessel within the patient's body such as a blood vessel in the patient's arm.

The housing 105 may house a catheter hub 110 and a needle hub 115. The catheter hub 110, in an embodiment, may be in the form of a button that may be actuated by the clinician as the clinician presses down on the catheter hub 110. The catheter hub 110 may include a fluidic channel 160 that fluidically couples a catheter 140 formed in the catheter hub 110 to a fluidic reservoir (not shown) via tubing 120. The fluidic channel may be, in an embodiment, a tube itself or may be a hollow portion within the catheter hub 110 that fluidically couples the catheter 140 to the tubing 120. During actuation of the catheter hub 110, the fluidic channel 160 may remain in fluidic communication with the catheter 140 and tubing 120 so as to allow a blood sample to pass through the catheter 140, fluidic channel 160, and tubing 120 or allow infusing fluids, such as a saline solution, various medicaments, and parenteral nutrition to pass through the tubing 120, fluidic channel 160, and catheter 140. The catheter 140, fluidic channel 160, and tubing 120 may cooperate to allow any fluid to pass into and out of the patient's blood stream with the patient's blood vessels.

The housing 105 may further house a needle hub 115. The needle hub 115 may include, in an embodiment, a needle 145. The needle 145 may be placed coaxially with the catheter 140 of the catheter hub 110. In an embodiment, the needle 145 may have a length longer than that of the catheter 140. The longer needle 145 may also include a bevel formed at a distal end of the needle 145. The bevel may allow the needle 145 and catheter 140 to pass through a patient's body and into a target blood vessel with the patient's body.

In an embodiment, the length of the needle 145 and catheter hub 110 may be long enough so as to reach a blood vessel within the patient's body when the needle hub 115 and catheter hub 110 are actuated by the clinician. In an embodiment, the length of the needle 145 may be between ¼ of an inch and an inch, inclusive. In an embodiment, the length of the needle 145 may be between 0.1 inches and 1 inch, inclusive.

The housing 105 may further include a layer of adhesive 130 formed on a bottom surface of the housing 105. The layer of adhesive 130 may be any type of adhesive that helps to maintain the intravenous therapy system 100 on the surface of the patient's body on, at least, a semi-permanent basis. Additionally, the layer of adhesive 130 may seal the interface between the patient's body and the intravenous therapy system 100 from any bacteria, viruses, or other contaminants that may come into contact with the location on the patient's body where the catheter 140 and needle 145 have interfaced into the patient's body. During operation, the site where the intravenous therapy system 100 is to interface with the patient's body may be disinfected using a disinfecting swab prior to application of the intravenous therapy system 100 to the patient's body. In an embodiment, the layer of adhesive 130 may be infused with a disinfection solution that continually provides a disinfection layer between the remaining portions of the patient's body and the location on the patient's body where the catheter 140 and needle 145 have interfaced into the patient's body.

The needle hub 115 may further include an adhesive-defeating fluid port 135. The adhesive-defeating fluid port 135 may be a port formed through the housing 105 of the intravenous therapy system 100 and into a location between the patient's body and the bottom surface of the housing 105. This location may include the location on the patient's body where the catheter 140 and needle 145 have interfaced into the patient's body. In an embodiment, the adhesive-defeating fluid port 135 may receive an adhesive-defeating fluid that dissolves or otherwise renders inert, the layer of adhesive 130 allowing the housing 105 of the intravenous therapy system 100 to be removed from the surface of the patient's body. The adhesive-defeating fluid may, in the embodiments herein, provides for a relatively less painful removal of the housing 105 of the intravenous therapy system 100 from off of the patient's body.

The needle hub 115, in an embodiment, may include a visual indicator 125. In the embodiment presented in FIG. 1, the visual indicator 125 is formed on the needle hub 115. However, the present specification contemplates that the visual indicator 125 is formed on any visible surface on the intravenous therapy system 100. The visual indicator 125, in an embodiment, may be a flashback indicator that includes a window that shows a spot of blood indicating that the needle 145 and catheter 140 have accessed a blood vessel within the patient's body. In an embodiment, the flashback comprises a small amount of blood, which flows from within the needle's lumen, through a channel formed in the needle hub 115 or catheter hub 110, and into a space at an outer surface of the needle hub 115, catheter hub 110, or other surfaces on the housing 105. As blood continues to flow proximally through the catheter, during operation of the intravenous therapy system 100, and into the tubing 120, the clinician may see the active flow of blood and may then be able to confirm that the distal tip of the needle 145 and/or catheter 140 is still within the patient's blood vessel. If, however, in an embodiment, the clinician observes that blood has stopped flowing into the catheter and/or the needle 145, the clinician may determine that the distal tip of the needle 145 or catheter 140 has been pushed completely through the blood vessel or out of the blood vessel. In response to this observation, the clinician may reposition the intravenous therapy system 100 and reinsert the needle 145 and catheter 140 until blood begins to flow into the catheter and needle 145 via confirmation at the visual indicator 125.

In an embodiment, the intravenous therapy system 100 may include a vibration device (not shown). The vibration device may be automatically activated upon actuation of the catheter hub 110 and needle hub 115 by the clinician. In this embodiment, the vibration device may vibrate the needle 145 and catheter 140 during insertion of the catheter 140 and needle 145 upon actuation of the catheter hub 110 and needle hub 115 by the clinician. The vibration of the catheter 140 and needle 145 may reduce or minimize the pain felt by the patient during insertion.

During operation of the intravenous therapy system 100, a clinician may position the housing 105 of the intravenous therapy system 100 onto the surface of a patient's skin at a location where a blood vessel is located. As described herein, a window formed in the housing 105 may allow a clinician implementing the intravenous therapy system 100 to see through the housing and to a patient's skin in order to align the housing 105 at an injection location over a blood vessel within the patient's skin. The clinician may then actuate the catheter hub 110 and needle hub 115 to cause the needle 145 and catheter 140 to be inserted into the patient's body to gain fluidic access to the patient's blood vessel. In an embodiment, the catheter hub 110 and/or needle hub 115 may include a bistable locking mechanism (not shown). The bistable locking mechanism may selectively lock the catheter hub 110 and/or needle hub 115 within the housing 105 in the actuation position. Upon further actuation of either of the catheter hub 110 or needle hub 115 by the clinician, the catheter hub 110 and needle hub 115 may remove the catheter 140 and needle 145, respectively, from within the patient's body and blood vessel. During operation, in an embodiment, the needle 145 may be removed coaxially from within the catheter 140 so that the catheter 140 may remain within the patient's blood vessel. In an embodiment, the needle hub 115 may be subsequentially actuated by the clinician, unlocking the needle hub 115 from the bistable locking mechanism, and removing the needle 145 coaxially from within the catheter 140. The needle hub 115 may further be allowed to, in an embodiment, be removed entirely from within the housing 105 and the needle 145 and needle hub 115 may be disposed of at a sharp disposal depository. Alternatively, the needle hub 115 may be prevented from being removed from the housing 105 so that the needle 145 may be kept within the housing 105 preventing any accidental pricking of the patient or other persons near the patient by the needle 145.

In an embodiment, the catheter 140 and needle 145 may be fluidically coupled to an infusion fluid port 155 and a bladder fluid injection port 150. The infusion fluid port 155 may interface with a reservoir maintaining an infusing fluid, such as a saline solution, various medicaments, and parenteral nutrition for introduction of those fluids through the intravenous therapy system 100 and into the patient's bloodstream. In an embodiment, the infusion fluid port 155 may share the same fluidic path to the needle 145 and catheter 140 via the tubing 120 with the bladder fluid injection port 150. In another embodiment, the fluidic path of the infusion fluid port 155 to the catheter 140 and needle 145 may be different from that of the bladder fluid injection port 150.

Figure 2:
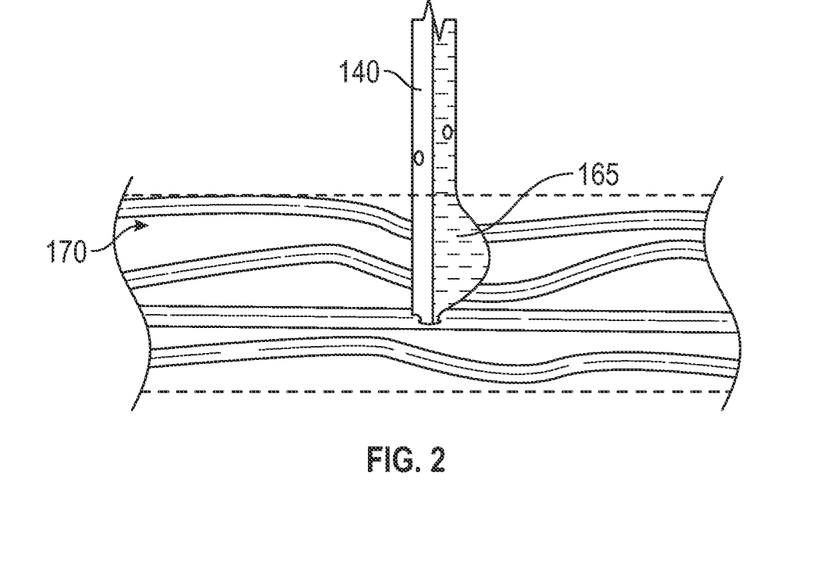
FIG. 2 is a side, cross-sectional view of a catheter of an intravenous therapy system within a blood vessel of a patient's body according to an embodiment of the present disclosure.

In an embodiment, the bladder fluid injection port 150 may be fluidically coupled to a bladder formed on the catheter 140. Turing to FIG. 2, FIG. 2 is a side, cross-sectional view of a catheter 140 of an intravenous therapy system 100 within a blood vessel 170 of a patient's body according to an embodiment of the present disclosure. The bladder 165 may be made of any elastic material that may receive a fluid therein to expand the bladder 165. FIG. 2 shows the bladder in an inflated or semi-inflated state with an amount of fluid maintained therein. As described herein in connection with FIG. 1, the bladder 165 may be fluidically coupled to a fluid source via a bladder fluid injection port 150 formed on the tubing 120. In the embodiment where the bladder fluid injection port 150 and infusion fluid port 155 share the same tubing 120 into the intravenous therapy system 100, the bladder 165 may be inflated using the same fluid used to infuse the patient's blood stream such as a saline solution.

During operation, the clinician may cause the needle 145 and catheter 140 to be injected into the patient's body and, specifically, blood vessel 170 by actuating the needle hub 115 and catheter hub 110, respectively. When the clinician has determined that the needle 145 and catheter 140 have accessed the blood vessel 170, the clinician may cause an amount of fluid to pass from the bladder fluid injection port 150, through the housing 105 of the intravenous therapy system 100 and into the bladder 165 formed around the catheter 140. By inflating the bladder 165 with the fluid, the catheter 140 may be maintained and secured within the patient's blood vessel 170 during a blood draw process or fluid infusion process as described herein. In an embodiment, the bladder 165 may be formed around an entire distal end of the catheter 140. In an embodiment, the bladder 165 may be formed around a portion of the distal end of the catheter 140.

Figure 3:
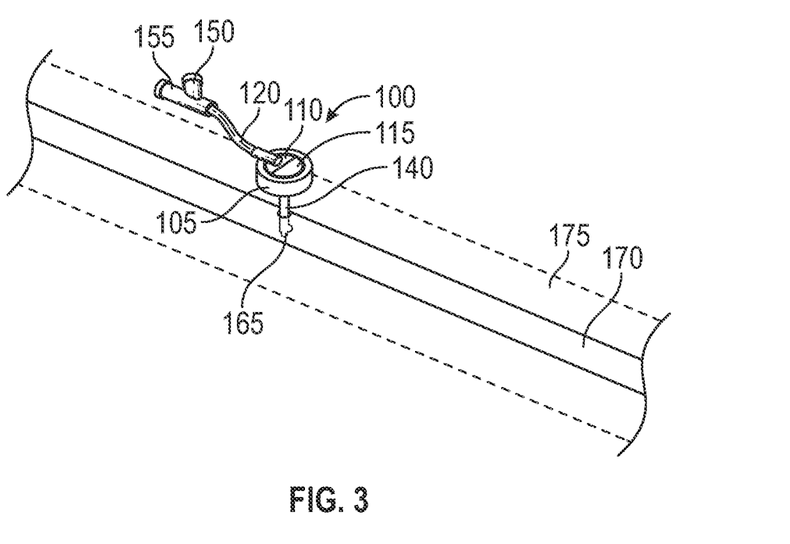
FIG. 3 is a perspective view of an intravenous therapy system placed at a patient's body according to an embodiment of the present disclosure.

FIG. 3 is a perspective view of an intravenous therapy system 100 placed at a patient's body 175 according to an embodiment of the present disclosure. FIG. 3 specifically shows the needle hub 115 and catheter hub 110 of the intravenous therapy system 100 in an actuated state. This actuated state may, in an embodiment, cause the catheter hub 110 and needle hub 115 to lie flush with a surface formed on the housing 105. This may indicate to a clinician that the catheter 140 and needle 145 of the catheter hub 110 and needle hub 115, respectively, have been fully deployed. As described herein, the catheter 140 further includes a bladder 165 that, when inflated with a fluid, maintains, at least, the catheter 140 within a blood vessel 170 within the patient's body 175. The bladder 165 may be inflated during use of the housing 105 against the patient's body 175, using any type of fluid. In the present specification and in the appended claims, the term "fluid" is meant to be understood as any substance that has not fixed shape and yields to external pressure. In the embodiments presented herein, the fluid may include a gas or a liquid.

Figure 4A:
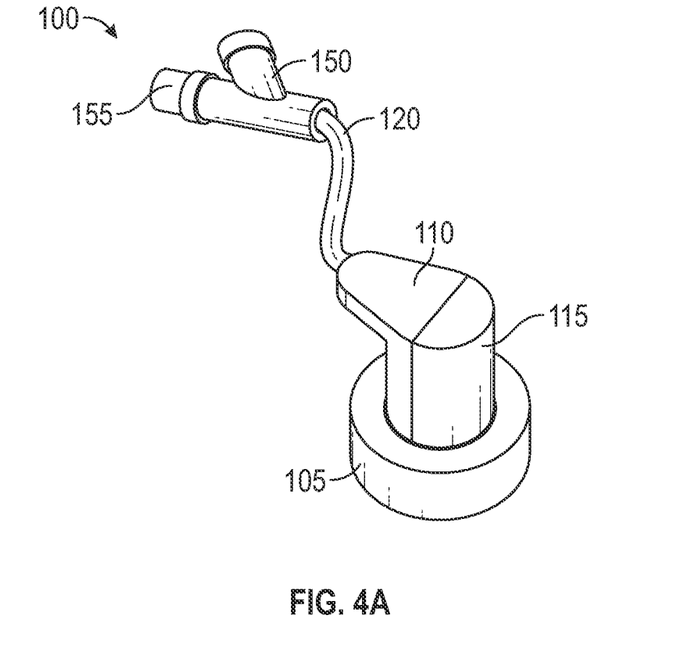
FIG. 4A is a perspective view of an intravenous therapy system in an un-actuated state according to an embodiment of the present disclosure.
Figure 4B:
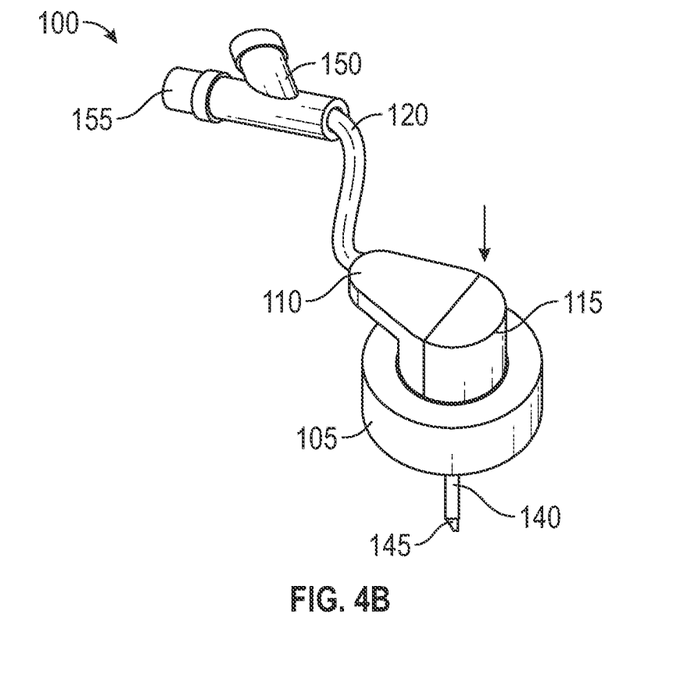
FIG. 4B is a perspective view of an intravenous therapy system in an actuated state according to an embodiment of the present disclosure.
Figure 4C:
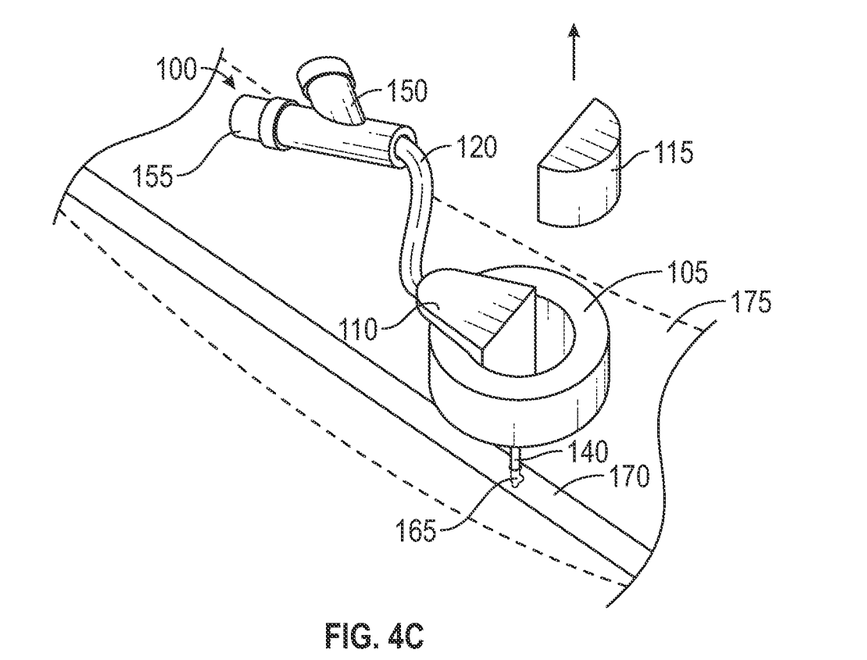
FIG. 4C is a perspective view of an intravenous therapy system in a semi-actuated state according to an embodiment of the present disclosure.

FIG. 4A is a perspective view of an intravenous therapy system in an un-actuated state according to an embodiment of the present disclosure. FIG. 4B is a perspective view of an intravenous therapy system in an actuated state according to an embodiment of the present disclosure. FIG. 4C is a perspective view of an intravenous therapy system in a semi-actuated state according to an embodiment of the present disclosure. FIGS. 4A through 4C may, in an embodiment, be seen as a process of actuation and use of the catheter hub 110 and needle hub 115 of the intravenous therapy system 100.

Starting with FIG. 4A, the intravenous therapy system 100 with its housing 105 may be placed on a patient's body 175 in an un-actuated state with the catheter hub 110 and needle hub 115 not being pressed down by the clinician. As described herein, the housing 105 may include a layer of adhesive (not shown) on a bottom surface of the housing 105 to secure the intravenous therapy system 100 to the patient's body 175.

Continuing with FIG. 4B, the intravenous therapy system 100 is shown after the clinician has actuated the catheter hub 110 and needle hub 115. The actuation of the catheter hub 110 and needle hub 115 (as indicated by an arrow) causes the catheter 140 and needle 145, respectively, to pass through the patient's body 175 and into a blood vessel 170.

FIG. 4C further shows that, upon insertion of the catheter 140 into the blood vessel 170 and, in an embodiment, retraction of the needle 145, the needle hub 115 may be removed from within the housing 105 (per arrow) of the intravenous therapy system 100 and the needle hub 115 with its needle 145 may be thrown away. In an embodiment, the needle hub 115 may be maintained within the housing 105 with the needle hub 115 retracted so that the needle 145 remains within the housing 105 and away from potentially pricking the patient, clinician, or other person.

Figure 5:
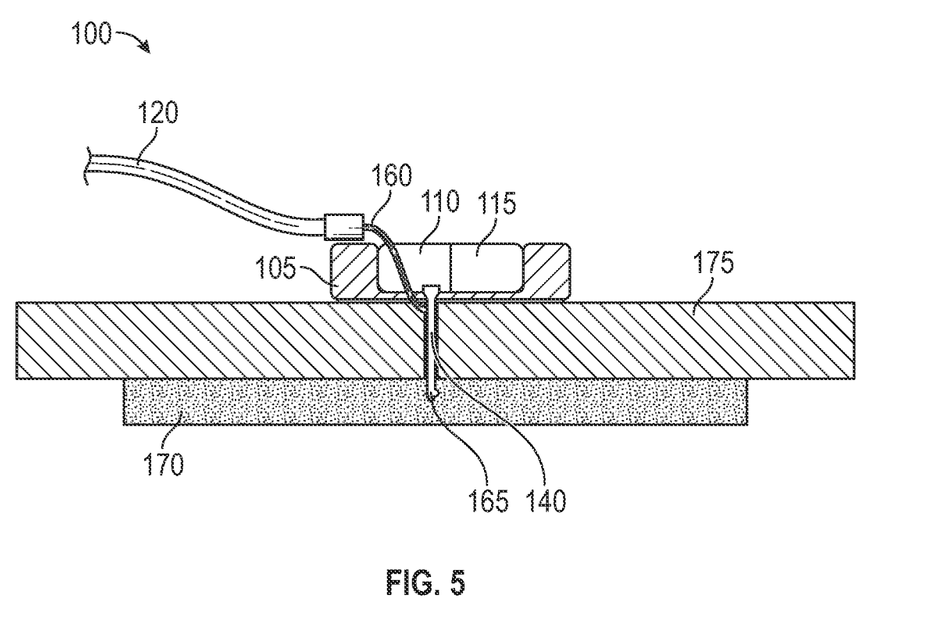
FIG. 5 is a side, cross-sectional view of the intravenous therapy system interfacing with a blood vessel according to an embodiment of the present disclosure.

FIG. 5 is a side, cross-sectional view of the intravenous therapy system 100 interfacing with a blood vessel 170 according to an embodiment of the present disclosure. The blood vessel 170 accessed by the catheter 140 of the intravenous therapy system 100 may be at any location along the patient's body 175. In this embodiment, the actuation of the catheter hub 110 and needle hub 115 introduces the catheter 140 and coaxial needle 145 into the blood stream of the blood vessel 170.

FIG. 5 also depicts that inflation of the bladder 165 by a fluid. The inflation of the bladder 165, as described herein, secures the catheter 140 against an interior surface of the blood vessel 170 and creating a bracing force against movement of the housing 105 of the intravenous therapy system 100 away from the patient's body 175.

During actuation of the catheter hub 110 and/or needle hub 115, the fluidic channel 160 may be maintained despite the movement of the catheter hub 110 and/or needle hub 115. As described herein, the needle hub 115 may be retracted from within the hollow of the catheter 140. In order to prevent fluid from leaking within the housing 105 of the intravenous therapy system 100, the needle 145 may be retracted to a location where the needle 145 does not interfere with the flow of fluid through the fluidic channel 160 and catheter 140 but also maintaining a seal within the outer surfaces of either the fluidic channel 160 or catheter 140. The bevel formed in the distal end of the needle 145 may allow for the fluid to pass by the needle 145 while the needle 145 prevents leakage of the fluids out of the catheter 140 and/or fluidic channel 160.

Figure 6:
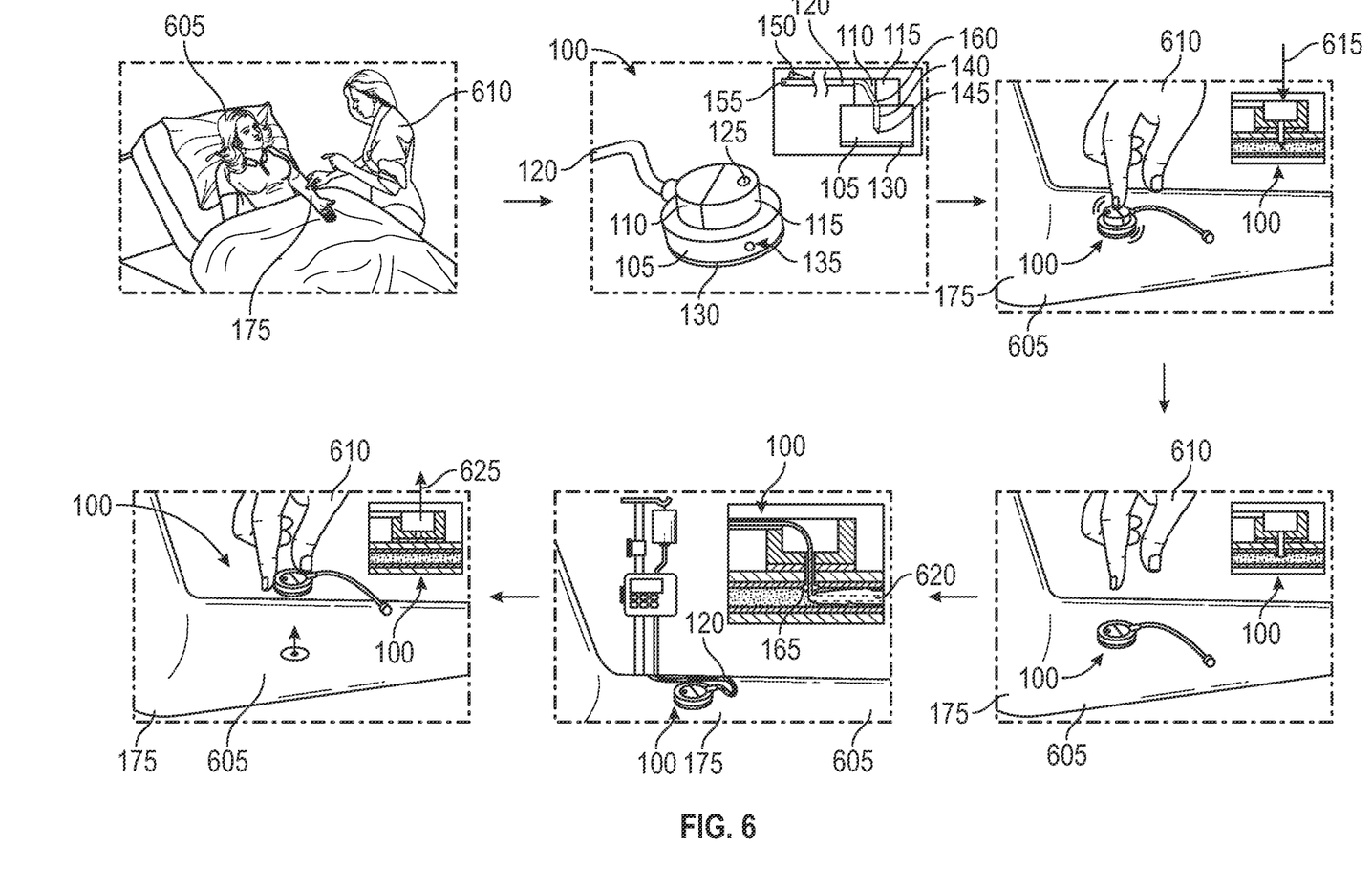
FIG. 6 is a flow diagram illustrating a method of operating an intravenous therapy system according to an embodiment of the present disclosure.

FIG. 6 is a flow diagram illustrating a method of operating an intravenous therapy system 100 according to an embodiment of the present disclosure. The flow diagram shows a number of panels showing actions by a clinician during use of the intravenous therapy system 100. In a first panel at the leftmost top of FIG. 6, the clinician 610 may address a location on the body of the patient 605 where a blood vessel is located such as, in this embodiment, an arm of the patient 605.

The flow diagram may proceed with at the center, top panel. The center, top panel shows that preparation of the intravenous therapy system 100 with the catheter hub 110 and needle hub 115 in an unactuated position. With the placement of the intravenous therapy system 100 and the needle 145 being hidden therein, the needle 145 may be kept from view by the patient's 605 view thereby easing any anxiety the patient may feel during a blood draw or infusion process.

The flow diagram, at the top, right-most panel, further shows the intravenous therapy system 100 applied to the patient's body 175. In this embodiment, the clinician 610 is actuating (arrow 615) the catheter hub 110 and needle hub 115. In an embodiment, the intravenous therapy system 100 may include a vibration device (not shown) that vibrates the needle 145 and catheter 140 during insertion of the catheter 140 and needle 145 upon actuation of the catheter hub 110 and needle hub 115 by the clinician. The vibration of the catheter 140 and needle 145 may reduce or minimize the pain felt by the patient during insertion. In this panel, it is also noted that the clinician 610 may control the speed of insertion of the catheter 140 and needle 145 by controlling how fast the catheter hub 110 and needle hub 115 are pressed.

The flow diagram further shows in a bottom, right-most panel, a cross section of the intravenous therapy system 100 with a bladder 165 coupled to the catheter 140 being inflated. As described herein, the bladder fluid injection port 150 may be fluidically coupled to a bladder formed on the catheter 140. The bladder 165 may be made of any elastic material that may receive a fluid therein to expand the bladder 165. The bladder, in an inflated or semi-inflated state, may maintain an amount of fluid therein. As described herein in connection with FIG. 1, the bladder 165 may be fluidically coupled to a fluid source via a bladder fluid injection port 150 formed on the tubing 120. In the embodiment where the bladder fluid injection port 150 and infusion fluid port 155 share the same tubing 120 into the intravenous therapy system 100, the bladder 165 may be inflated using the same fluid used to infuse the patient's blood stream such as a saline solution. In these embodiments, the clinician 610 may initiate and control the passing of fluid into the bladder 165 per this panel. Additionally, in this panel, the needle 145 may be retracted back into the housing 105 as described herein by re-actuation of the needle hub 115.

The flow diagram also shows, in a center, bottom panel, a cross-sectional view of the intravenous therapy system 100 showing a fluid 620 infusion into a blood vessel 170 within the patient's body 175. At this point, the patient 605 may remain still so that the fluid 620 may be infused. As described herein, the bladder 165 may maintain the housing 105 against the patient's body 175 adding, along with the layer of adhesive 130, further securement of the housing 105 to the patient's body 175.

The flow diagram also shows in a bottom, left-most panel, the removal of the intravenous therapy system 100 when the infusion or blood sampling process is completed. The clinician 610 may cause the fluid passed into the bladder 165 to be retracted therefrom by implementing, for example, a syringe at the bladder fluid injection port 150. The catheter 140 may also be retracted when the clinician 610 re-actuates (arrow 625) the catheter hub 110. As described herein, an adhesive-defeating fluid port 135 may be formed through the housing 105 of the intravenous therapy system 100 and into a location between the patient's body and the bottom surface of the housing 105. Here the adhesive-defeating fluid port 135 may receive an adhesive-defeating fluid that dissolves or otherwise renders inert, the layer of adhesive 130 formed at the bottom of the housing 105 and securing the housing 105 to the patient's body 175. This may allow the housing 105 of the intravenous therapy system 100 to be removed from the surface of the patient's body 175 by the clinician 610. The adhesive-defeating fluid may, in the embodiments herein, provides for a relatively less painful removal of the housing 105 of the intravenous therapy system 100 from off of the patient's body.

Figure 7:
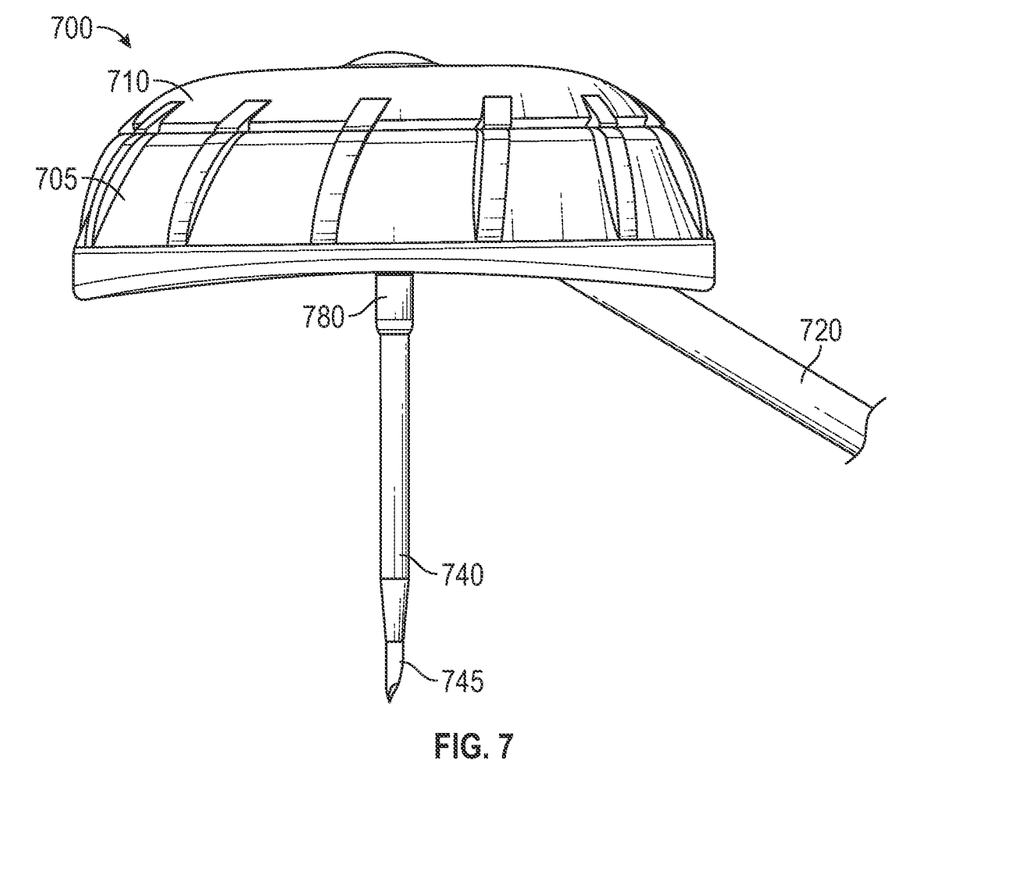
FIG. 7 is a side view of an intravenous therapy system within a blood vessel of a patient's body according to an embodiment of the present disclosure.

FIG. 7 is a side view of an intravenous therapy system 700 within a blood vessel of a patient's body according to an embodiment of the present disclosure. The intravenous therapy system 700 may include a housing 705 that forms a rigid casing used to house the components of the intravenous therapy system 700. The housing 705, in an embodiment, may be made of a plastic that reduces the weight of the intravenous therapy system 700. In an embodiment, a portion of the housing 705 may be made of a translucent plastic that allows a clinician or other health care provider (HCP) to see through a portion of the intravenous therapy system 700 and to the skin or surface of a patient's body. In this embodiment, the translucent plastic may specifically allow the clinician to align the intravenous therapy system 700 with a blood vessel within the patient's body such as a blood vessel in the patient's arm.

The housing 705 may house a catheter and needle hub 710. The catheter and needle hub 710, in an embodiment, may be in the form of a cap that may interface, mechanically, with the housing 705 so that the catheter and needle hub 710 may interface with the housing 705 at a specific orientation. The catheter and needle hub 710 may include a fluidic channel (not shown) that fluidically couples a needle 745 and catheter 740 coupled to the catheter and needle hub 710 to a fluidic reservoir (not shown) via a tubing 720. The fluidic channel may be, in an embodiment, a tube itself or may be a hollow portion within the catheter hub 710 that fluidically couples the catheter 740 and needle 745 to the tubing 720. During operation of the intravenous therapy system 700, the fluidic channel may remain in fluidic communication with the catheter 740 and needle 745 and tubing 720 so as to allow a blood sample to pass through the catheter 740 and/or needle 745, fluidic channel, and tubing 720 or allow infusing fluids, such as a saline solution, various medicaments, and parenteral nutrition to pass through the tubing 720, fluidic channel, and needle 745 and catheter 740. The catheter 740, fluidic channel, and tubing 720 may cooperate to allow any fluid to pass into and out of the patient's blood stream with the patient's blood vessels.

In an embodiment, the needle 745 may be formed coaxially within the catheter 740. During operation of the intravenous therapy system 700, in an embodiment, a clinician or other HCP may interface the catheter and needle hub 710 with the housing 705 either prior to or after the housing 705 has been positioned on the patient's body. Where the catheter and needle hub 710 is interfaced with the housing 705 prior to application of the intravenous therapy system 700 onto the patient's skin, the needle 745 and catheter 740 may be placed on the surface of the patient's skin and the clinician may ply pressure to cause the needle 745 to puncture the skin and enter the patient's blood vessel as described herein. Where the intravenous therapy system 700 is applied to the surface of the patient's skin prior to the catheter and needle hub 710 being interfaced with the housing 705, the clinician may align the housing 705 such that the needle 745 and catheter 740 will intersect with a patient's blood vessel when the catheter and needle hub 710 is interfaced with the housing 705. The clinician may then interface the catheter and needle hub 710 with the intravenous therapy system 700 and apply pressure to the catheter and needle hub 710 to cause the needle 745 to puncture the patient's skin and enter the blood vessel.

As the catheter and needle hub 710 interface with the housing 705, the needle 745 and catheter 740 may interface with a catheter coupler 780. The catheter coupler 780 may be a gasket that seals the interface between the housing 705 and the catheter 740 and needle 745. In an embodiment, the catheter coupler 780 may be a separate part from the catheter 740 and needle 745. In an embodiment, the catheter coupler 780 may form a part of the catheter 740. The catheter coupler 780 may, in an embodiment, allows for the catheter 740 and needle 745 to move slightly allowing for some degrees of freedom.

In an embodiment, the catheter and needle hub 710 may include an interface surface 785. The interface surface 785 may be a portion of the catheter and needle hub 710 that provides a keyed fit into the housing 705 of the intravenous therapy system 700 such that any other orientation of the catheter and needle hub 710 relative to the housing 705 would not allow the catheter and needle hub 710 to interface with the housing 705. In an embodiment, the catheter and needle hub 710 may be provided to a clinician coupled to the housing 705 of the intravenous therapy system 700 so that the needle 745 and catheter 740 are not exposed until the intravenous therapy system 700 is introduced at the patient's body.

Figure 8:
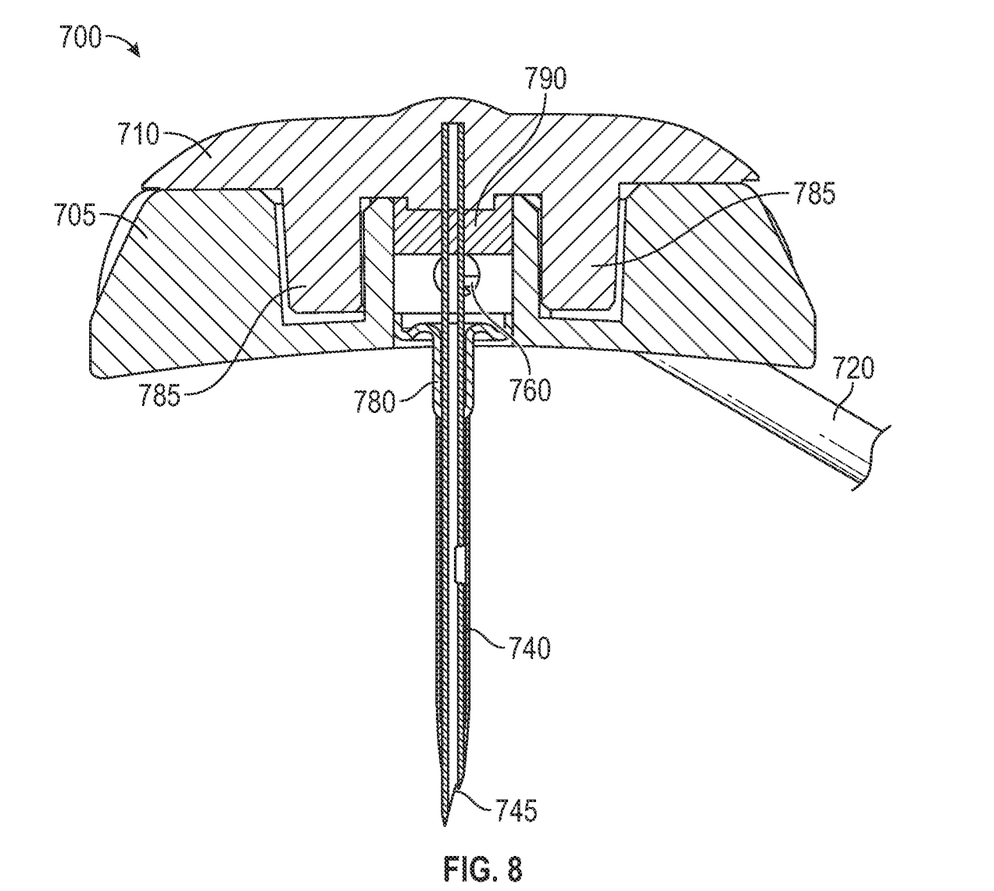
FIG. 8 is a side, cross-sectional view of an intravenous therapy system according to an embodiment of the present disclosure.

FIG. 8 is a side, cross-sectional view of an intravenous therapy system 700 according to an embodiment of the present disclosure. FIG. 8 shows the fluidic coupling of the tubing 720 to the fluidic channel 760. In an embodiment, the needle 745 and catheter 740 may include a via through which fluids may pass to and from the fluidic channel 760 and tubing 720. This via may be placed within the portion of the housing 705 where the fluidic channel 760 interfaces with the needle 745 and catheter 740.

In an embodiment, the needle 745 and catheter and needle hub 710 may be removed from within the patient such that the catheter 740 remains within the patient's blood vessel. In this embodiment, the catheter and needle hub 710 may include a removable seal that seals a proximal end of the catheter 740 to atmosphere after removal of the catheter and needle hub 710.

In an embodiment, the housing 705 may have a bottom surface that is curved. The curvature may be formed to conform to a surface of the patient's body to which the intravenous therapy system 700 is to be affixed to. In an embodiment, the bottom surface of the intravenous therapy system 700 may include an adhesive to temporarily couple the intravenous therapy system 700 to the patient's body. Similar to FIG. 1, in an embodiment, the intravenous therapy system 700 may include an adhesive-defeating fluid port to receive an adhesive-defeating fluid to reduce the adhesive effects of the adhesive during removal of the intravenous therapy system from the patient's skin.

In an embodiment, the housing 705 of the intravenous therapy system 700 may include a septum 790. The septum 790 may be placed to fluidically isolate a terminal or distal end of the fluidic channel 760 within the housing 705 from atmosphere. During operation, the needle 745 and catheter 740 of the catheter and needle hub 710 may be passed through the septum 790 and through the housing 705 as illustrated in FIG. 8 while the septum 790 maintains the fluidic seal between the terminal end of the fluidic channel 760 and atmosphere.

Figure 9:
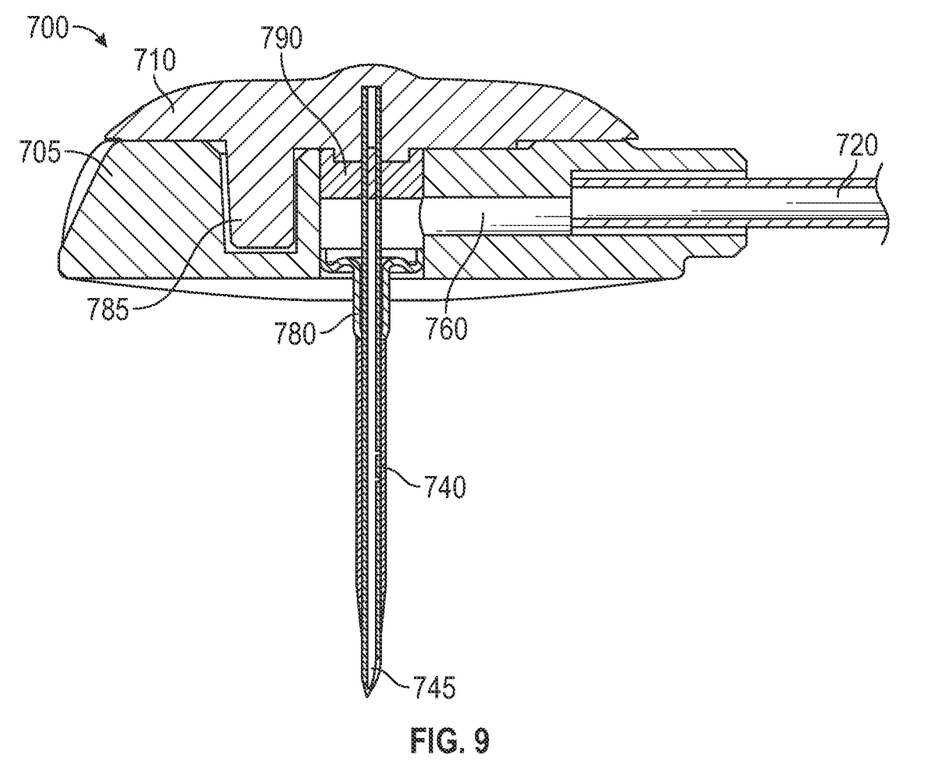
FIG. 9 is a side, cross-sectional view of an intravenous therapy system according to an embodiment of the present disclosure.

FIG. 9 is a side, cross-sectional view of an intravenous therapy system 700 according to an embodiment of the present disclosure. The side, cross-sectional view of the intravenous therapy system 700 shown in FIG. 9 is a 90 degree rotation of the intravenous therapy system 700 illustrated in FIG. 8 rotated along a longitudinal axis of the needle 745 and catheter 740.

FIG. 9 illustrates the fluidic coupling of the fluidic channel 760 with the tubing 720. In this embodiment, the fluidic channel 760 is formed as a hollow tube formed through the housing 705 of the intravenous therapy system 700. In an embodiment, the fluidic channel 760 may be a tube that fluidically couples the tubing 720 to a via formed through the needle 745 and catheter 740 as described herein.

The intravenous therapy system 700 includes a catheter coupler 780. In an embodiment, the catheter coupler 780 prevents fluids from leaking out of the intravenous therapy system 700 by fluidically sealing the interface between the intravenous therapy system 700 and the outer surface of the catheter 740. In an embodiment, the catheter and needle hub 710 may include an interface surface 785. In an embodiment, the interface surface 785 may be a portion of the catheter and needle hub 710 that provides a keyed fit into the housing 705 of the intravenous therapy system 700 such that any other orientation of the catheter and needle hub 710 relative to the housing 705 may not allow the catheter and needle hub 710 to interface with the housing 705. In an embodiment, the catheter and needle hub 710 may be provided to a clinician coupled to the housing 705 of the intravenous therapy system 700 so that the needle 745 and catheter 740 are not exposed until the intravenous therapy system 700 is introduced at the patient's body.

In an embodiment, the housing 705 of the intravenous therapy system 700 may include a septum 790. The septum 790 may be placed to fluidically isolate a terminal or distal end of the fluidic channel 760 within the housing 705 from atmosphere. During operation, the needle 745 and catheter 740 of the catheter and needle hub 710 may be passed through the septum 790 and through the housing 705 as illustrated in FIG. 9 while the septum 790 maintains the fluidic seal between the terminal end of the fluidic channel 760 and atmosphere.

Figure 10:
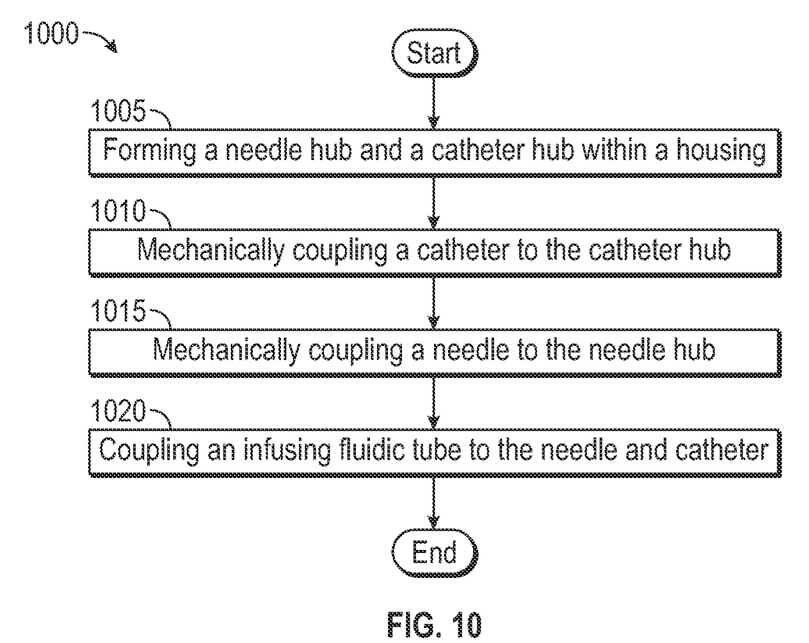
FIG. 10 is a flowchart depicting a method of manufacturing an intravenous device according to some embodiments of the present disclosure.

FIG. 10 is a flowchart depicting a method 1000 of manufacturing an intravenous device according to some embodiments of the present disclosure. The method 1000 may include, at block 1005, forming a needle hub and a catheter hub within a housing. The catheter hub may, in an embodiment, be in the form of a button that may be actuated by the clinician as the clinician presses down on the catheter hub. The catheter hub may include a fluidic channel that fluidically couples a catheter formed in the catheter hub to a fluidic reservoir via tubing. The fluidic channel may be, in an embodiment, a tube itself or may be a hollow portion within the catheter hub that fluidically couples the catheter to the tubing. The catheter, fluidic channel, and tubing may cooperate to allow any fluid to pass into and out of the patient's blood stream with the patient's blood vessels.

The needle hub may include, in an embodiment, a needle. The needle may be placed coaxially with the catheter of the catheter hub. In an embodiment, the needle may have a length longer than that of the catheter. The longer needle may also include a bevel formed at a distal end of the needle. The bevel may allow the needle and catheter to pass through a patient's body and into a target blood vessel with the patient's body. In an embodiment, the length of the needle and catheter hub may be long enough so as to reach a blood vessel within the patient's body when the needle hub and catheter hub are actuated by the clinician. In an embodiment, the length of the needle may be between ¼ of an inch and an inch, inclusive. In an embodiment, the length of the needle 145 may be between 0.1 inches and 1 inch, inclusive.

The method 1000 may further include, at block 1010, mechanically coupling a catheter to the catheter hub. As described herein the catheter may continue a passageway or tube formed in catheter hub so as to provide for a fluidic channel from a tubing, through the needle hub, and to the catheter.

The method 1000 may further include, at block 1015, mechanically coupling a needle to the needle hub. The needle may be placed coaxially with the catheter so that the catheter and needle may be introduced into the patient's body concurrently.

The method 1000 may also include, at block 1020, coupling an infusing fluidic tube to the needle and catheter. The fluidic tube may be the tubing described in connection with FIG. 1.

Again, it is understood that the embodiments of the present application may be combined. As an example, the embodiments of FIGS. 1-7 may be arranged to fit specific uses based on the type of action being conducted. For example, where a blood vessel is to be accessed by the needle, the intravenous therapy system may be located above the vein for quick and less painful insertion of the catheter and needle. The catheter angle may vary from perpendicular in some embodiment, and this variation will not fully inhibit the viability of the intravenous therapy system described herein to access a patient's blood vessel and maintain that access. The insertion motion and speed may vary based on the actuation motion of the clinician. At the conclusion of insertion, the needle may be removed in a manner similar to existing catheter system or, alternatively, the needle may be captured in the intravenous therapy system 100 throughout the infusion or blood draw process thereby eliminating the need for removal of the needle. A window formed in the housing of the intravenous therapy system may be used to aid the clinician in the health assessment process described herein. Additionally, insertion-specific blood flashback may be incorporated into the intravenous therapy system through the use of the visual indicator described herein. These features provide for an intravenous therapy system that reduces the physical trauma to the patient's body while reducing the anxiety of the patient during deployment.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous therapy system, comprising:
    a housing to house an actuation hub, the actuation hub comprising:
        a needle hub operatively coupled to a needle to insert the needle into a body of the patient; and
        a catheter hub fluidically coupled to a catheter to insert the catheter into the body, the catheter being formed coaxially with an outer surface of the needle;
    an inflatable bladder formed along a length of the catheter to maintain the catheter in the body; and
    a fluidic channel in fluid communication with both the inflatable bladder and the catheter hub such that the fluidic channel is configured for inflation of the inflatable bladder with a first fluid and infusion of a second fluid into a blood stream of the patient, wherein the first fluid and the second fluid are the same fluid;
    wherein after insertion of the needle into the body, the needle is configured to be retracted into the needle hub, thus maintaining a distal end of the needle within the needle hub, to coaxially remove the needle from within the catheter, wherein after insertion of the needle into the body, the needle is configured to be retracted into the needle hub such that the needle does not interfere with the flow of fluid through the fluidic channel to the inflatable bladder and the catheter hub but also maintains a seal to prevent leakage out of the catheter or the fluidic channel.

2. The intravenous therapy system of claim 1, wherein after insertion of the needle into the body, the needle hub and the needle may be removed from the actuation hub.

3. The intravenous therapy system of claim 1, further comprising a bladder fluid injection port to couple a fluid reservoir to the inflatable bladder via a length of tubing, wherein the fluidic channel extends through the length of tubing.

4. The intravenous therapy system of claim 1, further comprising a visual indicator to indicate when the needle and the catheter have accessed a blood vessel within the body.

5. The intravenous therapy system of claim 1, further comprising an adhesive formed on a bottom surface of the housing to secure the intravenous therapy system to a skin of the patient.

6. The intravenous therapy system of claim 5, further comprising an adhesive-defeating fluid port to receive an adhesive-defeating fluid to reduce adhesive effects of the adhesive during removal of the intravenous therapy system from the skin.

7. The intravenous therapy system of claim 1, further comprising a window to allow a clinician implementing the intravenous therapy system to see through the housing and to a patient's skin.

8. The intravenous therapy system of claim 1, wherein the needle hub and the catheter hub further comprise a locking mechanism that selectively locks and unlocks the needle hub and the catheter hub in an actuated position.

9. A peripheral intravenous catheter (PIVC), comprising:
    a circular housing to house:
        a needle hub operatively coupled to a needle to insert the needle into a body of a patient; and
        a catheter hub operatively coupled to a catheter to insert the catheter into the body, the catheter being formed coaxially with an outer surface of the needle, wherein after insertion of the needle into the body, the needle is configured to be retracted into the needle hub, thus maintaining a distal end of the needle within the needle hub, to coaxially remove the needle from within the catheter;
    an inflatable bladder formed along a length of the catheter to maintain the catheter in the body; and
    a fluidic channel in fluid communication with both the inflatable bladder and the catheter hub such that the fluidic channel is configured for inflation of the inflatable bladder with a first fluid and infusion of a second fluid into a blood stream of the patient, wherein the first fluid and the second fluid are the same fluid,
    wherein after insertion of the needle into the body, the needle is configured to be retracted into the needle hub such that the needle does not interfere with the flow of fluid through the fluidic channel to the inflatable bladder and the catheter hub but also maintains a seal to prevent leakage out of the catheter or the fluidic channel.

10. The PIVC of claim 9, further comprising a visual indicator to indicate when the needle and the catheter have accessed a blood vessel within the patient's body.

11. The PIVC of claim 9, further comprising a window to allow a clinician implementing the PIVC to see through the housing and to a patient's skin.

\* \* \* \* \*